United States Patent
Samoszuk et al.

(10) Patent No.: US 6,720,144 B1
(45) Date of Patent: Apr. 13, 2004

(54) DETECTION OF CLONAL T-CELL RECEPTOR-γ GENE REARRANGEMENT BY PCR/TEMPORAL TEMPERATURE GRADIENT GEL ELECTROPHORESIS (TTGE)

(75) Inventors: Michael Samoszuk, Rancho Santa Margarita, CA (US); Dan Zhu, Irvine, CA (US)

(73) Assignee: Quest Diagnostics, San Juan Capistrano, CA (US)

(*) Notice: Subject to any disclaimer, the term of this patent is extended or adjusted under 35 U.S.C. 154(b) by 0 days.

(21) Appl. No.: 09/886,227

(22) Filed: Jun. 21, 2001

(51) Int. Cl.[7] ............................ C12Q 1/68; C12P 19/34; C07H 21/02

(52) U.S. Cl. ...................... 435/6; 435/91.2; 435/91.21; 435/91.5; 536/23.1; 536/24.3; 536/24.31; 536/24.33

(58) Field of Search ................. 435/6, 91.1, 91.2; 536/23.1, 24.3, 24.31

(56) References Cited

PUBLICATIONS

Shina et al, Letters in Applied Microbiology, (Jun. 2001) 32:384–387.*
Chott et al, "The same dominant T cell clone is present in multiple regressing skin lesions and associated T cell lymphomas of patients with lymphomatoid papulosis", J. Invest. Dermatology, (1996) vol. 106, No. 4, pp. 696–700.*
Theodorou et al, "Cutaneous T–cell infiltrates: Analysis T–cell receptor gamma gene rearrangement by polymerase chain reaciton and denaturing gradient gel electrophoresis", Blood (1995) vol. 86, No. 1, pp. 305–310.*
Alkan et al, "Detection of T–cell Receptor–y Gene Rearrangement in Lymphoproliferative Disorders by Temperature Gradient Gel Electrophoresis," Arch. Pathol. Lab. Med., vol. 123, Feb. 2001, pp. 202–207.
Andersen et al, "Polymerase chain reaction–denaturing gradient gel electrophoresis (PCR/DGGE)–based detection of clonal T–cell receptor γ gene . . . " J. Cutan. Pathol. , vol. 26, Jan. 1999, pp. 176–182.
Bjørheim [a,b] et al, "Mutation analyses of KRAS exon 1 comparing 3 different techniques: temporal temperature Gradient electrophoresis, constant . . . ," Mutation Research, vol. 403, Jul. 1998, pp. 103–112.
Bourguin et al, "Rapid, nonradioactive detection of clonal T–cell receptor gene rearrangements in lympoid neoplasms," Proc. Natl. Acad. Sci. USA, vol. 87, Nov. 1990, pp. 8536–3540.
Chen et al, "Detection of Mitochondrial DNA Mutations by Temporal Temperature Gradient Gel Electrophoresis," Clinical Chemistry, vol. 45, 1999, pp. 1162–1167.
Coombs et al, "Optimisation of DNA and RNA extraction from archival formalin–fixed tissue," Nucleic Acids Research, vol. 27, 1999, pp. i–iii.

(List continued on next page.)

Primary Examiner—Jeffrey Fredman
(74) Attorney, Agent, or Firm—Foley & Lardner; Richard J. Warburg

(57) ABSTRACT

The present invention provides methods and compositions for detecting and analyzing clonal T-cell receptor (TCR) gene rearrangement using temporal temperature gradient gel electrophoresis (TTGE), which employs a gradual and uniform increase in the temperature of a constant denaturing gel to resolve different DNA molecules based on base pair composition. The present invention also provides methods and compositions for providing appropriate DNA migration markers for TTGE analysis.

1 Claim, 4 Drawing Sheets

OTHER PUBLICATIONS

Day et al, "Electrophoresis for genotyping: temporal thermal gradient gel electrophoresis for profiling of Oligonucleotide dissociation," Nucleic Acids Research, vol. 23, Jul. 1995, pp. 2404–2412.

Dereure et al, "T–Cell Clonality in Pityriasis Lichenoides et Varioliformis Acuta," Arch. Dermatol, vol. 136, Dec. 2000, pp. 1483–1486.

Farnleitner et al, "Comparative analysis of denaturing gradient gel electrophoresis and temporal temperature Gradient gel . . . " Letters in Applied Microbiology, vol. 30, 2000, pp. 427–431.

Flug et al, "T–cell receptor gene rearrangements as markers of lineage and clonality in T–cell neoplasms," Proc. Natl. Adad. Sci. USA, vol. 82, May 1985, pp. 3640–3464.

Garcia et al, "Emerging principles for T cell receptor recognition of antigen in cellular Immunity," Reviews in Immunogenetics, vol. 1, 1999, pp. 75–90.

Gill et al, "Immunoglobulin and T–cell Receptor Gene Rearrangement," Diagnostic Hematology, vol. 8, Aug. 1994, pp. 751–770.

Greiner, Timothy C., "Advances in Molecular Hematopathology, T–Cell Receptor γ and bcl–2 Genes," American Journal of Pathology, vol. 154, Jan. 1999, pp. 7–9.

Hafner et al, "Isothermal Amplification and Multimerization of DNA by Bst DNA Polymerase," BioTechniques, vol. 30, Apr. 2001, pp. 852–867.

Higashimoto et al, "Rapid Detection of FGFR Mutations in Syndromic Craniosynostosis by Temporal . . . ," International Journal of Laboratory Medicine and Molecular Diagnositcs, vol. 45, Nov. 1999, pp. 2005–2006.

Menke et al, "Temperature gradient gel electrophoresis for analysis of a polymerase chain reaction–based. diagnostic clonality assay in the early stages of cutaneous . . . ," Electrophoresis, vol. 16, 1996, pp. 733–338.

Murphy et al, "Detection of TCR–γ gene rearrangements in early mycosis fungoides by non–radioactive PCR–SSCP," J. Cutan. Pathol., vol. 27, 2000, pp. 228–234.

Orita et al, "Rapid and Sensitive Detection of Point Mutations and DNA Polymorphisms using the Polymerase Chain Reaction," Genomics, vol. 5, 1989, pp. 874–879.

Posnett et al, Clonal Populations of T Cells in Normal Elderly Humans: The T Cell Equivalent to "Benign Monoclonal Gammapathy," J. Exp. Med., vol. 179, Feb. 1994, pp. 609–618.

Raulet, David H., "The Structure, Function, and Molecular Genetics of the γ/δ T Cell Receptor," Ann. Rev. Immunol., vol. 7, 1989, pp. 173–207.

Saiki, Randal K., "Amplification of Genomic DNA," PCR Protocols: A Guide to Methods and Applications, vol. 2, 1990, pp. 13–20.

Schell et al, "Detection of point mutations by capillary electrophoresis with temporal temperature gradients," Electrophoresis, vol. 20, 1999, pp. 2864–2869.

Theodorou et al, "Cutaneous T–Cell Infiltrates: Analysis of T–Cell Receptor γ Gene Rearrangement by . . . ," Blood, vol. 86, Jul. 1995, pp. 306–310.

Vásquez et al, "Temporal temperature gradient gel electrophoresis (TTGE) as a tool for identification of Lactobacillus casei, *Lactobacillus paracasei*, . . . " Letters In Applied Microbiology, vol. 32, 2001, pp. 215–219.

Waldmann et al, "Rearrangements of Genes for the Antigen Receptor on T Cells as Markers of Lineage . . . ," The New England Journal of Medicine, vol. 313, Sep. 1985, pp. 777–783.

Wharam et al, "Specific detection of DNA and RNA targets using a novel isothermal nucleic acid amplification Assay based on the formation . . . ," Nucleic Acids Research, vol. 29, 2001, pp. 1–8.

Wiese et al, "Scanning for mutations in the human prion protein open reading frame by temporal temperature Gradient gel electrophoresis," Electrophoresis, vol. 16, Oct. 1995, pp. 1789–1984.

Wood et al, "Detection of Clonal T–Cell Receptor γ Gene Rearrangements in Early Mycosis Fungoides/Sezary Syndrome by Polymerase . . . ," Journal Investigative Dermatology, vol. 103, 1994, pp. 34–41.

Yanagi et al, "A human T cell–specific cDNA clone encodes a protein having extensive homology to Immunoglobulin chains," Nature, vol. 308, Mar. 1984, pp. 145–149.

Yoshino et al, "Temperature sweep gel electrophoresis: a simple method to detect point mutations," Nucleic Acids Research, vol. 19, 1991, p. 3153.

* cited by examiner

Figure 4.   Primers for Detection of Clonal T-Cell Receptor-γ Rearrangement

TcellJ-R (Jγ1/2):
5' cgc ccg ccg cgc ccc gcg ccc gtc ccg ccg ccc ccc TGT TCC ACT GCC AAA GAG TTT CTT 3'

TcellV-F (Vγ1-8):
5'-AGGGTTGTGTTGGAATCAGG-3'

TcellVγ9:
5' TAAATTCCAAATTCTTGGTTTA 3'

TcellVγ10:
5' CTC AAC AAA ATC CGC AGC TCG ACG CAG CA 3'

TcellVγ11:
5' CAA TCT CTG CTC AAG ATT GCT CAG GTG GG 3'

TcellVγ12:
5' ACT CTG CAG CCT CTT GGG CAC TGC TCT AAA 3'

DETECTION OF CLONAL T-CELL RECEPTOR-γ GENE REARRANGEMENT BY PCR/TEMPORAL TEMPERATURE GRADIENT GEL ELECTROPHORESIS (TTGE)

INTRODUCTION

This invention relates to the field of detecting a genetic marker of T-cell malignancies. The invention provides compositions and methods useful for detecting clonal T-cell receptor gene arrangements. By using PCR and temporal temperature gradient gel electrophoresis (TTGE), the clonality of T-cell populations in a sample can be determined.

BACKGROUND OF THE INVENTION

The following discussion of the background of the invention is merely provided to aid the reader in understanding the invention and is not admitted to describe or constitute prior art to the present invention.

T lymphocytes are important players in the immune response of mammalian organisms. Each T-lymphocyte has on its surface a molecule, known as the T-cell receptor ("TCR") that exhibits a specificity of binding to a target antigen that is similar to the specificity of binding exhibited by antibodies, and TCR is encoded by genes having an organization similar to that of antibody genes.

During normal T-cell development, each TCR gene (α, β, γ and δ) can rearrange, leading to highly diverse TCR proteins. Among the four TCR gene types, the TCR-γ genes are the first to rearrange. During the rearrangement of each TCR gene, one of its different variable (V) regions combines with one of its different joining (J) regions. In the TCR-γ gene, a few nucleotides (N region) are also inserted randomly into the VJ regions by terminal nucleotidyl tansferase (TdT), resulting in an increased sequence diversity in the TCR-γ gene as compared to the other TCR genes. It is believed that each mature T-cell possesses an individual sequence of rearranged TCR genes.

T-cell malignancies can present to the physician with strikingly similar clinical patterns to simple reactive, or inflanmatory, diseases. T-cell malignancies, however, can be differentiated from reactive diseases by the presence in malignancy of an overgrowth of a single, clonal, T-cell population. Therefore, analysis of TCR gene rearrangement, and particularly the TCR-γ gene, is of practical value in determining the clonality T-cell populations for the diagnosis and prognosis of T-cell malignancies (Flug et al., Proc Natl Acad Sci USA. 82: 3460–3464, 1985; Yanagi et al., Nature 308: 145–149, 1984; Waldmann et al., N Engl J Med 313: 776–783, 1985; Raulet, Annu Rev Immunol. 7: 175–207, 1989; Theodorou et al., Blood 86: 305–310,1995).

To date, numerous techniques have been used to analyze TCR gene rearrangement. Southern blotting hybridization was the first widely used technique (Spagnolo et al., Pathol. 26: 268–275, 1994). Because Southern blotting hybridization can be time-consuming and labor-intensive, and requires the use of large amounts of high molecular weight DNA and radioactivity, polymerase chain reaction (PCR)-based techniques have become more popular in research and clinical laboratories. These techniques can also permit the use of DNA extracted from formalin fixed parafin-embedded specimens and are more rapid than hybridization approaches (Theodorou et al., Blood 86: 305–310,1995; Murphy et al., J Cutan Pathol. 27: 228–234, 2000; Anderson et al, J. Cutan Pathol. 26: 176–182, 1999; Wood et a., J Invest Dermatol. 103: 34–41,1994; Menke etal., Electrophoresis 16: 733–738, 1995; Bourguin et al., Proc Natl Acad Sci USA. 87: 8536–8540, 1990).

PCR amplification of one or more TCR genes from non-malignant peripheral blood or lymph node tissue samples generates a mixture of multiple DNA molecules differing in size and/or base pair composition. Because the combinatorial and junctional diversity in TCR gene rearrangement is limited, the amplified products may be of similar length. Thus, the limited diversity may result in false clonal bands when analyzed by a standard gel electrophoresis methods that separate DNA molecules based solely on size (Theodorou et al., Blood 86: 305–310,1995; Menke et al., Electrophoresis 16: 733–738, 1995), and can occur when using either Southern blotting hybridization (which is based on agarose gel electrophoresis) or PCR followed by standard polyacrylamide gel electrophoresis (PAGE). Furthermore, due to the poor resolution of standard gel electrophoresis methods, DNA bands of low frequency clones may be lost in the polyclonal background "smear," leading to difficult in interpreting the results of such an analysis.

Recently, electrophoresis techniques that resolve DNA molecules based on size and base pair composition have been explored, such as polymorphism (SSCP) (Murphy et al., J Cutan Pathol. 27: 228–234, 2000), denaturing gradient gel electrophoresis (DGGE) (Theodorou et al., Blood 86: 305–310, 1995; Anderson et al., J. Cutan Pathol. 26: 176–182, 1999; Wood et al., J Invest Dermnatol. 103: 34–41, 1994) and temperature gradient gel electrophoresis (TGGE) (Menke et al., Electrophoresis 16: 733–738, 1995). To maximize the resolution of SSCP, however, more than one electrophoretic condition is often needed (Orita et al., Genomics 5: 874–879, 1989). Moreover, although DGGE has been gaining popularity to determine the clonality of T-cell populations (Theodorou et al., Blood 86: 305–310, 1995; Anderson et al., J. Cutan Pathol. 26: 176–182, 1999; Wood et al., J Invest Dermatol. 103:34–41, 1994), the difficulty in preparing denaturing gradient polyacrylamide gel limits the routine usage of this technique in clinical laboratories. Similarly, the routine use of TGGE in clinical laboratories is also limited because of its reliance on an instrument that is both expensive and difficult to maintain. (Menke et al. Electrophoresis. 16:733–738, 1995; Alkan et al. Arch Pathol Lab Med. 125:202–207, 2001).

Thus, there remains in the art a need for methods and compositions that can reproducibly and economically resolve clonal T-cell receptor populations in patient samples.

SUMMARY OF THE INVENTION

In the present invention provides methods and compositions to determine the clonality of T-cell receptor populations present in a sample. Temporal temperature gradient gel electrophoresis (TTGE), developed by Yoshino et al. (Nucleic Acids Res. 19:3153, 1991) and Chen et al. (Clin Chem. 45:1162–1167, 1999), can be used to detect the presence or absence of a clonal TCR gene rearrangement. In the instant methods, target DNA is electrophorcsed in a denaturing gel, and the temperature of the gel is increased gradually and uniformly across a range in which differences in the base composition of the target DNA are resolved. Because the gel itself is not a gradient gel, and because the temperature gradient is temporal rather than spatial across the gel, the instant methods can be performed in an economical fashion. In addition, the resulting DNA band patterns can be easily interpreted and quality controlled in a clinical laboratory setting.

In accordance with the present invention, TTGE can detect clonal TCR (e.g., TCR-γ) gene arrangements present in a sample at concentrations as low as one malignant T-cell among 100 normal cells. Additionally, DNA can be extracted from stored samples (e.g., samples stored at 4° C. for up to 7 days and at room temperature for up to 4 days) and used for PCR amplification to generate gene amplicons for TCR gene rearrangement analysis by TTGE without significant variability of the band pattern and signal intensity. Thus, the invention provides simple, accurate and sensitive techniques to diagnose and monitor patients with T-cell malignancies.

In a first aspect, the instant invention relates to methods for determining the clonality of a T-cell receptor (TCR) rearrangement in a sample comprising the steps of extracting nucleic acids from the sample; amplifying the nucleic acids, preferably by polymerase chain reaction with one or more TCR specific primers to provide one or more TCR DNA fragments; and analyzing amplified TCR DNA fragments using an electrophoretic gel by temporal temperature gradient gel electrophoreis (TTGE). The present of one or more discrete bands in the electrophoretic gel indicates the presence of a clonal TCR rearrangement.

In certain embodiments, the electrophoretic profile of a test sample can be compared to one or more control samples (e.g., a negative control sample obtained from a sample not containing a clonal T-cell rearrangement), and the presence of one or more discrete bands in the test sample that are not present in the control sample(s) indicates the presence of a clonal TCR rearrangement.

As used herein, the term "T-cell receptor" refers to the antigen-recognition molecules present on the surface of T-cells. See, e.g., Garcia et al., *Rev. Immunogenet.* 1999;1 (1):75–90. As indicated above, during normal T-cell development, each of the four TCR genes, α, β, γ and δ, can rearrange leading to highly diverse TCR proteins. See, e.g., Gill and Gulley, *Hematol. Onco Clin. North Am.* 1994 August;8(4):751–70; Greiner, *Am. J. Pathol.* 1999 January;154(1):7–9.

The term "clonality" as used herein regarding T-cells refers to the expansion of a single population of T-cells in a sample. Such a clonal expansion occurs when, for example, T-cell populations are challenged by an antigen. In response, that population of T-cells that recognize the antigen increase in number. In more dramatic fashion, clonal expansion occurs in certain T-cell malignancies, in which a single T-cell population expands beyond normal levels due to a loss of growth control in a T-cell. In certain embodiments, clonality is determined by analyzing a TCR-α, TCR-β, TCR-γ and/or TCR-δ gene rearrangement using PCR amplification with two or more appropriate primer sequences for the gene(s) of interest, and temporal temperature gradient gel electrophoresis, as described herein The term "amplify" with respect to nucleic acid sequences refers to methods that increase the representation of a population of nucleic acid sequences in a sample. Nucleic acid amplification methods, such as PCR, isothermal methods, rolling circle methods, etc., are well known to the skilled artisan. See, e.g., Saiki, "Amplification of Genomic DNA" in PCR *Protocols*, Innis et al., Eds., Academic Press, San Diego, Cailf. 1990, pp 13–20; Wharam et al., *Nucleic Acids Res.* Jun. 1, 2001;29(11):E54—E54; Hafner et al., *Biotechniques* 2001 April;30(4):852–6, 858, 860 passim; Zhong et al., *Biotechniques* 2001 April;30(4):852–6, 858, 860 passim.

In preferred embodiments, generic DNA representing a TCR gene is extracted from a cell and amplified; however, other nucleic acids (e.g., mRNA) may also be extracted and amplified to perform the clonality assays of the present invention.

In certain embodiments, nucleic acids can be amplified using PCR with TCR-specific primers, i.e., oligonucleotides suitable for amplifying specific regions of TCR Preferred primers are Vγ1–8 (5'-AGGGTTGTGTTGGAATCAGG-3') (SEQ ID NO:3) for V region and Jγ½ (5'-CGCCCGCCGCGCCCCGCGCCCGTCCCGC-CGCCCCCCTGTTCCACTGCCAAA GAGTTTCTT-3') (SEQ ID NO:4) for J region. The primer sequence for Jγ½ for J region is a GC-clamp region designed to introduce a high melting point domain at one end of the PCR amplicons, facilitating analysis by TTGE. Additional suitable primers are described below in the figures.

As used herein, the term temporal temperature gradient gel electrophoresis ("TTGE") refers to electrophoresis methods in which samples are run in a gel matrix, e.g., a polyacrylamide gel, and the temperature of the gel is altered in a time-dependent fashion as the samples are migrating through the gel. In such a gel, the relative mobility of a DNA sample is based on its relative thermal stability. Thus, by careful selection of the temperature profile of the gel, the migration of molecules in the sample can be altered as the temperature changes. For example, DNA molecules can be run in the gel matrix using a temperature profile in which certain base pairs in the molecules "melt;" that is, where the temperature is sufficient to disrupt the hydrogen bonding in the Watson-Crick base pairs. The skilled artisan will understand that different DNA sequences will have different relative thermal stability; e.g., A-T-rich regions will melt at a lower temperature than G_C-rich regions. As the base pairs melt, the molecular structure of the DNA becomes locally "open," resulting in a change in mobility.

The term "gel" as used herein refers to any semisolid medium capable of supporting a fluid phase for separating nucleic acids based on size and melting temperature profile of the individual nucleic acid molecules when an electric field is placed across the medium. Gels may include starch, acrylamide, agarose, or mixtures of these materials, and may be a single concentration, or gradient. The electrolyte used to separate materials in a gel may be either continuous or discontinuous. In preferred embodiments, the gel is an acrylamide gel of a single concentration throughout, and the elecrolyte is a continuous buffer system.

Typical etectrophoresis gels comprise a plurality of channels, known to the artisan as "lanes," in which individual samples (and/or controls) may be loaded and run in parallel on the same gel. Because all such samples are exposed to essentially the same electrophoresis conditions, the characteristics of samples (and/or controls) in different lanes can be directly compared. Molecules that migrate to the same location in the gel appear, upon detection, as "bands;" i.e., a line of material about the width of the lane and having a characteristic height (often about 0.2 to about 5 mm). Bands on separate gels can often be compared by determining the relative location of the band in relation to controls ("standards") that have been run in each of the separate gels.

Material will migrate to the same location in the gel for a number of reasons, depending on the type of electrophoresis used. For example, in isoelectric focusing, material will migrate to the same location if the material has the same isoelectric point. As discussed herein, in TTGE, DNA molecules will migrate at the same rate, and thus migrate to the same location in a gel, if the molecules have the same relative thermal stability.

As used herein, the term "the presence one or more discrete bands" refers to a signal that is obtained from molecules that migrate to a discrete location in an electrophoretic gel. For example, a clonal T-cell rearrangement in a malignancy can be detected as a population of DNA molecules that migrate at identical rates through a gel, such that they appear as a single "band" upon detection, e.g., by gel staining techniques well known in the art. As discussed herein, because genes are "multiallelic;" that is, there are two alleles of each gene, one on each chromosome of a chromosome pair, a clonal T-cell rearrangement may appear as more than one discrete band in such a gel.

Preferably, a discrete band provides a signal that is twice the background signal 3 times the background signal, 4 times the background signal, 5 times the background signal, 7.5 times the background signal, 10 times the background signal, 15 times the background signal, 20 times the background signal, 50 times the background signal, 100 times the background signal, and 500 times the background signal, where the background signal is obtained from a negative control sample or from an area of the electrophoresis lane containing diffuse staining.

Additionally, a discrete band can be discriminated from a diffuse "smear" within a gel by a sharp fall off in intensity present at the band boundary, where signal intensity rapidly falls to background. This rapid fall-off results in a band that is between $1/10^{th}$ and twice the height of a band obtained from a positive standard run in the same gel, while diffuse staining results in a band that is greater than twice the height of the positive standard.

The term "sample" as used herein refers to any liquid or solid material believed to comprise T-cells. In preferred embodiments, a sample is a tissue sample from an animal, most preferably a human. Preferred sample tissues of the instant invention include, but are not limited to, plasma, serum, whole blood, blood cells, lymphatic fluid, lymphatic cells, lymph node tissue, cerebrospinal fluid, and skin or other organs (e.g., biopsy material). Such sample tissues may or may not be fixed, e.g., by formalin, and/or embedded for sectioning, e.g., in paraffin.

The term "patient sample" as used herein refers to a sample from an animal, most preferably a human, seeking diagnosis or treatment of a disease.

In another aspect, the present invention relates to methods for diagnosing a patient suspected of having a neoplastic T-cell disease. In these methods, a clonal expansion of a T-cell population is determined by analyzing the clonality of TCR gene rearrangements in a sample. A positive indication of such a clonal expansion is indicative of a neoplastic T-cell disease. These methods preferably comprise obtaining a sample from a patient and determining whether a clonal TCR gene rearrangement is present in the sample using TTGE, wherein the presence of a discrete band in the electrophoretic gel indicates the presence of a clonal TCR rearrangement.

In certain embodiments, these methods can be used to compare two or more lesions in a patient having a neoplastic T-cell disease. As used herein, the term "lesion" refers to diseased tissue in a patient. In these embodiments, a sample from a first lesion and a second lesion in the patient can be obtained, and each sample can be analyzed for the presence or absence of identical clonal TCR gene rearrangements in each sample. In various preferred embodiments, the lesions can be obtained from the same disease focus, but at different times during the course of a disease (e.g., before and after a treatment regimen); or from different disease foci at the same or different times. As used herein, the term "disease focus" refers to a spatially unique location in a patient that harbors diseased tissue.

In yet another aspect, the present invention relates to methods and compositions for designing a treatment regimen. In these methods, the presence or amount of a clonal TCR gene rearrangement in a patient following a selected treatment(s) can be used to assess the success or lack thereof in the treatment regimen. Such methods can also compare the relative presence or amount of a clonal TCR gene rearrangement in a patient before and after such a treatment regimen.

Similarly, the present invention also relates to methods and compositions for screening therapeutic compounds. In these methods, the presence or amount of a clonal TCR gene rearrangement in a patient following administration of one or more compounds can be used to assess therapeutic efficacy. Such methods can also compare the relative presence or amount of a clonal TCR gene rearrangement in a patient before and after administration of one or more compounds.

In accordance with still another aspect, the present invention relates to methods for preparing a substantially pure nucleic acid migration marker for use in a TTGE gel, and to the nucleic acid migration markers themselves. Preferably, such a marker can be prepared from one or more DNA fragments having known migration rates in the TTGE gel. For example, a standard DNA ladder for TTGE analysis can be made by amplifying one or more DNA fragments containing known TCR rearrangements using TCR-specific primers. Alternatively, synthetic methods well known to the skilled artisan can be used to prepare such a marker.

In either case, the DNA fragments can then be inserted into a plasmid cloning vector. The plasmid can then be used to transform a cell population in order to amplify the number of plasmid molecules, thus preparing "plasmid amplicons." Isolated plasmids and/or amplicons can be used to generate a large number of DNA migration markers, e.g., by PCR using TCR-specific primers.

In certain embodiments, the plasmids and/or amplicons containing known TCR rearrangements can be subjected to PCR in parallel with samples to be analyzed for clonal TCR rearrangement, using identical conditions and TCR-specific primers. In these embodiments, the plasmid amplicons can both provide both DNA migration markers and a positive PCR control, in which the presence of the DNA migration marker in the TTGE gel confirms that the PCR reaction successfully occurred in the samples.

Mixtures of a plurality of TTGE migration markers can provide multiple reference points in a TTGE gel. Thus, in preferred embodiments, a composition of migration markers comprises 2, 3, 4, 5, 6, 7, 10, and 20 different migration markers in a buffer suitable for loading on a TTGE gel.

The term "migration marker" as used herein refers to a nucleic acid sequence known to migrate with a certain relative mobility in a TTGE gel and form a discrete band in the gel. The term "substantially pure" as used herein regarding TTGE migration markers refers to a purity sufficient to provide such a discrete band on a TTGE gel.

and PCR/TTGE (lower panel). PCR/PAGE displayed ambiguous results; M: 100 bp DNA size marker; PSL: positive standard ladder; Lanes 1,3,4,5 and 7: Samples showing clonal band patterns on TTGE; Lanes 2,6,8 and 9: Samples showing polyclonal smear on TTGE; The sample in lane 1 showed multiple clonal bands which may represent biallelic TCR-γ gene rearrangement at the analyzed regions or multi-clonal evolution; N: negative standard DNA; P: positive standard DNA.

Figure 3:
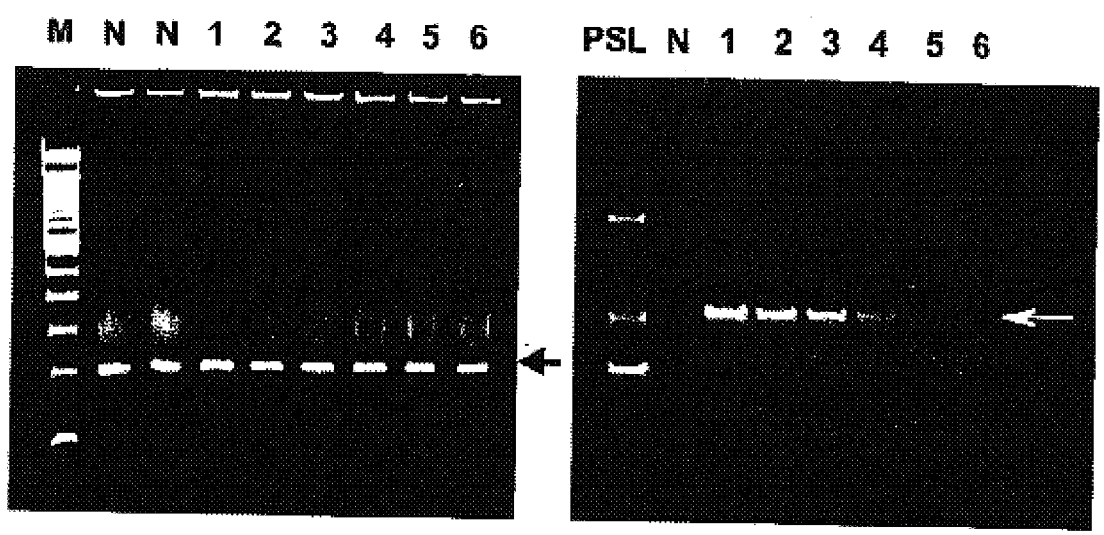

FIG. 3 depicts a comparison between PCR/PAGE and PCR/TTGE using a clonal TCR-γ gene rearrangement positive sample serially diluted two-fold with negative standard DNA. Left panel: PCR/PAGE result; Right panel PCR/TTGE result; M: 100 bp DNA size marker, PSL: positive standard ladder; N: Known negative standard DNA; Lanes 1–6: a positive sample 2,4,8,16,32 and 64 folds diluted respectively with negative standard DNA. On PAGE gel, the negative DNA PCR product showed false clonal band and the serially diluted samples did not show significant changes in signal intensity suggesting that PCR/PAGE is likely to give inaccurate results.

FIG. 4 depicts preferred primers for detection of clonal T-cell receptor-γ rearrangement.

DETAILED DESCRIPTION OF THE INVENTION

The present invention provides methods for determining the clonality of a T-cell receptor gene arrangement in a sample analyzed by temporal temperature gradient gel electrophoresis (TTGE). The present invention also provides methods for producing a DNA migration marker for TTGE analysis.

T-cell clonality is an essential feature of T-cell malignancy, although several reports show that clonal T-cell populations may be detected in certain benign conditions such as lymphomatoid papulosis and pityriasis lichenoides acuta (PLEVA) (Posnett et al., J Exp Med. 179:609–618, 1994) and in the blood of some elderly patients (Dereure et a., Arch Dermatol. 136:1483–1486, 2000). While this suggests that T-cell clonality by itself may not be diagnostic of T-cell malignancy, it does provide a key diagnostic marker for evaluation by the clinician to distinguish lymphoma from reactive lymphoproliferation.

Analysis of T-cell clonality has been underutilized due to difficulties in methodology and interpretation of results. Size-based electrophoresis techniques give poor separation that fails to resolve TCR gene amplicon molecules with the same length but different base pair compositions. Consequently false positive results are obtained by using these assays (Theodorou et at., Blood 86:305–310, 1995; Anderson et al., J, Cutan Pathol. 26: 176–182, 1999; Menke et al., Electrophoresis 16: 733–738, 1995). For example, samples known to be negative may often display a light band (FIGS. 1 and 2) which may be a mixture of different TCR gene molecules with the same length or non-specific PCR noise.

Moreover, for samples with relatively low proportions of monoclonal T-cells, the determination of positivity depends on comparison of band intensity between the sample and the negative control. Since the band intensity varies with several factors, including sample load variations, a subjective determination based on band intensity is likely to give inaccurate results, leading to false negative results as well.

Sample Preparation

As discussed herein, the expansion of a single population of T-cells in a sample can be determined by examining TCR-α, TCR-β, TCR-γ and/or TCR-δ genes for the presence of a clonal DNA rearrangement. Thus, any liquid or solid material believed to comprise T-cells can be an appropriate sample. Preferred sample tissues include plasma, serum, whole blood, blood A cells, lymphatic fluid, lymnphatic cells, lymph node tissue, cerebrospinal fluid, and skin or other organs (e.g., biopsy material), but T-cells are widely distributed throughout the body.

Such samples will often be taken from patients suspected of having a T-cell malignancy. T-cell malignancies include T cell prolymphocytic leukaemia; T-cell large granular lymphoproliferative (LGL) disorder, mycosis fungoides; Sezazy type cutaneous lymphoma; Erythrodermic type cutaneous lymphoma; peripheral T cell lymphoma; angioimnmunoblastic T cell lymphoma; enteropathy-type T cell lymphoma; adult T cell lymphomaaleukaemia (ATLUL); La and anaplastic large cell lymphoma (ALCL), CD30+, T and null-cell types.

For example, cutaneous T-cell lymphoma develops slowly over many years, and may initially present as itchy, dry patches of skin that may be redder, darker or lighter than normal. These patches may later thicken into raised plaques. As more and more of the skin becomes involved, the skin may become infected. The disease can spread to lymph nodes or to other organs in the body, such as the spleen, lungs or liver. At these various stages of the disease, each lesion may be an appropriate sampling location.

Nucleic acids (DNA or RNA) representing the TCR gene of interest may be extracted from fresh tissue, or from tissue that has been fixed, e.g., by formalin, and/or embedded for sectioning, e.g., in paraffin, as is often the case for clinical pathology samples. See, e.g., Coombs et al., Nucleic Acids Research, 27, e12—e12, 1999. Additionally, various commercial nucleic acid purification kits, such as Puregene™ (Gentra Systems), Generation® (Gentra Systems), and Purescript® (Gentra Systems) are known to the skilled artisan.

Amplification of the TCR Sequence

Once DNA has been isolated from a tissue sample, the target TCR-α, TCR-β, TCR-γ and/or TCR-δ genes may be amplified by various in vitro methods. See, e.g., Wharaarn el al., *Nucleic Acids Res.* Jun. 1 2001;29(11):E54—E54; Hafner el al., *Biotechniques* 2001 April;30(4):852–6, 858, 860 passim; Zhong et al., *Biotechniques* 2001 April;30(4): 852–6, 858, 860 passim.

Preferably, PCR is used to amplify the TCR sequence. In this method, two or more oligonucleotide primers that flank a and bind to opposite strands of a DNA fragment of interest are repetitively annealed to their complementary sequences, extended by a DNA polymerase, and heat denatured, resulting in exponential amplification of the target DNA sequence. The skilled artisan is capable of designing and preparing probes that are appropriate for amplifying a target sequence. A number of suitable probes are described in FIG. 3. Cycling parameters can be varied, depending on the length of DNA to be extended.

Preferably, at least one of the amplification probes comprises a G-C rich "clamp" region. As discussed herein, the instant methods rely on increasing temperature in the gel to "melt" regions of double-stranded TCR DNA sequences, which result in a characteristic mobility for each amplified gene sequence (urunelted DNA, being more compact, will run faster through a gel; as the DNA becomes more "open," migration is retarded). If a double-stranded TCR DNA sequence were to become completely melted, however, the size of the resulting single-stranded fragment, and its resulting mobility in the gel, would not be in scale with the remaining double-stranded fragments. The G-C clamp, because of its high melting point (>90° C.), prevents any fragments from melting to single strands under the typical electrophoretic conditions employed.

TTGE

For TTGE, the critical parameters include concentrations of denaturants (e.g., urea and/or formamide), starting and ending temperatures, temperature ramp rate and running time. All of those needed to be optimized computationafly and empirically in order to achieve maximal separation, and hence resolution, based on the thermal properties of the target DNA molecule. Various computer programs are known in the art for estimating the melting point of a DNA fragment under a given set of electrophoretic conditions (e.g., MacMelt, WinMelt (Bio-Rad)). Typically, the presence of any G-C clamp region is ignored in performing this calculation. The addition of denaturants can be expected to lower the theoretical melting point by about 1° C. for every 3% denaturant (100%=7 M Urea+40% formamide). In certain TTGE apparatuses, the temperature of the gel is increased by immersing the gel cassette in a buffre tank, and gradually increasing the temperature of the buffer. In such an apparatus, the running time necessary for a given gel can be estimated by ETEB–STEB/RR (hours), where ETEB=end temperature of the electrophoresis buffer; STEB=start temperature of electrophoresis buffer; and RR=ramp rate. While a linear ramp rate is often used, the temperature gradient can be designed as a non-linear gradient as well (e.g., a series of discrete steps, or a concave or convex gradient).

Suitable conditions can be selected from the following:

| | |
|---|---|
| Polyacrylamide gel: | 5–20% polyacrylamide; |
| Urea: | 5–8 M |
| Formamide: | 0–10% v/v |
| Temperature Range: | 10–80° C. |
| Temperature Ramp Rate: | 0.5–5°/hr |

A clonal T-cell rearrangement in a malignancy can be detected as a population of DNA molecules that migrate at identical rates through a TTGE gel, such that they appear as one or more discrete bands upon detection. Because genes are multiallelic, a clonal T-cell rerrangement may appear as more than one discrete band in such a gel. Target DNA can be detected in the gel by numerous methods known in the art For example, primers and/or bases used for extension can be isotopically, fluorescently, or enzymatically labeled, either directly or indirectly (e.g., by the use of biotinylated nucleotides). Alternatively, various DNA stains (e.g., ethidium bromide) can be used to directly visualize the target DNA.

TTGE Migration Markers

Because the TTGE methods of the instant invention separate based on both size and thermal stability of a nucleic acid molecule, simple size markers may not provide useful information when included on a gel. Furthermore, size markers may not run at a reproducible position when run in separate gels, thus complicating the comparison of the gels. An improved standard DNA ladder for TTGE analysis can be made by providing one or more DNA fragments having a predetermined melting profile. The use of such TTGE migration markers is not limited to the analysis of TCR rearrangements, but rather may be used in any electrophoretic technique where the separation of nucleic acid molecules is temperature dependent.

Such fragments can be designed de novo, or can be made by amplifying one or more DNA fragments containing known TCR rearrangements using TCR-specific primers. For example, samples from patients known to have a clonal T-cell proliferation can serve as sources of DNA for the generation of migration standards by PCR as discussed above. Alternatively, synthetic methods well known to the skilled artisan can be used to prepare such a marker. The markers can pemit different gels to be correlated to one another by comparing the migration distance of a sample band to that of size markers that have been run in both gels. Such "relative mobility" methods are well known in the art.

The DNA fragments produced for use as migration markers can then be inserted into a plasmid cloning vector for additional amplification. Methods and tools for insertion, deletion, and manipulation of DNA are well-known to a person of ordinary skill in the art. See, *Molecular Cloning, a Laboralory Manual*, 2nd Ed., 1989, Sambrook, Fritsch, and Maniatis, Cold Spring Harbor Laboratory Press.

Additionally, because plasmids and/or amplicons containing known TCR rearrangements can be amplified with the same primers used for the sample of interest, the migration markers can also serve as positive PCR controls by be subjected to PCR in parallel with samples to be analyzed for clonal TCR rearrangement.

EXAMPLES

Example 1

Clinical Samples

Forty-two clinical samples tested for clonal TCR-γ gene rearrangement were analyzed by the PCR/PAGE and PCR/TTGE methods. Thirty samples were peripheral blood samples and twelve samples were formalin-fixed paraffin-embedded skin biopsies and lymph node tissues. The clinical diagnosis for each sample was not available at the time of sample analysis. After the samples were analyzed by both methods, the clinical correlation for T-cell clonality of these samples was obtained.

Example 2

DNA Extraction

DNA from peripheral blood and formalin-fixed paraffin-embedded tissues was purified using standard methods.

For peripheral blood samples, a white blood cell pellet was prepared through histopaque centrifugation and extracted with 1 ml DNAzol® (Molecular Research Center, Inc., Cincinnati, Ohio, USA) at room temperature for 5 minutes. The supernatant was collected, mixed with 0.5 ml ethanol and incubated at room temperature for 5 minutes. After centrifugation, the DNA pellet was washed twice with 75% ethanol, air-dried and dissolved in 200 µl ddH$_2$O;

For formalin-fixed tissues, three to ten 10 µm thick sections were prepared for each sample based on the sample size, digested with an appropriate amount of extraction buffer (50 mM Tris, 2mM EDTA, 0.5% Tween 20 and 200 µl/ml proteinase K) at 56° C. for 3 hours and then incubated at 96° C. for 10 minutes to inactivate the proteinase. The supernatant was collected through centrifugation and extracted using an equal volume of phenol/chloroform. DNA was precipitated by mixing the aqueous phase with $1/20^{th}$ volume of 5M NaCl and 2.5×volume of ethanol and incubating at −20° C. for 30 minutes. After centrifugation, the DNA pellet was obtained, air-dried and dissolved in an appropriate amount of ddH$_2$O. The DNA samples extracted from blood were quantified using a spectrophotometer and the concentrations are adjusted to approximately 200 ng/µl.

Example 3

Polymerase Chain Reaction (PCR)

PCR for TCR-γ was performed in a 55 µl volumne containing 5 µl extracted DNA, 1×PCR Buffer II (Perkin. Elmer), 2 mM MgCl$_2$, 200 µl each of dNTPs, 1.25 U AmpliTaq DNA polymerase and 227 nM each of two primers. Rearranged TCR-γ gene was amplified using primers Vγ1–8 (5'-AGGGTTGTGTTGGAATCAGG-3') (SEQ ID NO:3) for V region and Jγ½ (5'-CGCCCGCCGCGCCCCGCGCCCGTCCCGC-CGCCCCCCTGTTC CACTGCCAAAGAGTTTCTT-3') (SEQ ID NO:4) for J region to analyze the most common VJγ recombination types for method comparison between PCR/PAGE and PCR/TTGE. The underlined primer sequence of Jγ½ for J region is a GC-clamp region which is designed to introduce a high melting point domain at one end of the PCR amplicon. This facilitates analysis by TTGE.

Each DNA sample was also amplified by PCR with HLA primers (forward: 5'-GTGCTGCAGGTGTAAACTTGTACCAG-3' (SEQ ID NO:1) and reverse: 5'-CACGGATCCGGTAGCAGCGGTAGAGTTG-3') (SEQ ID NO:2) to serve as an internal control to verify successful DNA isolation and the presence of amplifiable DNA.

The amplification was started by incubation at 95° C. for 5 minutes followed by 10 cycles each composed of 95° C. for 1 minute, 60° C. for 1 minute and 72° C. for 1 minute, then 25 cycles each composed of 95° C. for 20 seconds, 55° C. for 30 seconds and 72° C. for 20 seconds, and finally elongation at 72° C. for 10 minutes.

Example 4

Gel Electrophoresis

The success of the PCR reaction was verified by running 10 µl of the TCR-γ and HLA PCR products for each sample on a 2% agarose gel. PCR amplification for the HLA gene showed a single band of 242 bp for all 42 specimens. Amplification with TCR-γ gene specific primers showed a single band of approximately 200 bp for Vγ1–8 +Jγ½ amplicons.

Ten microliters of the amplified TCR-γ gene product were mixed with equal amount of loading buffer (0.05% Bromophenol Blue, 0.05% Xylene Cyanol, 70% Glycerol) and analyzed by 8% Novex mini polyacrylamide gel (PAGE) from Invitrogen (Carlsbad, Calif., USA) and by temporal temperature gradient gel electrophoresis (TTGE) using the DCode™ System from Bio-Rad Laboratories (Hercules, Calif., USA).

Figure 1:
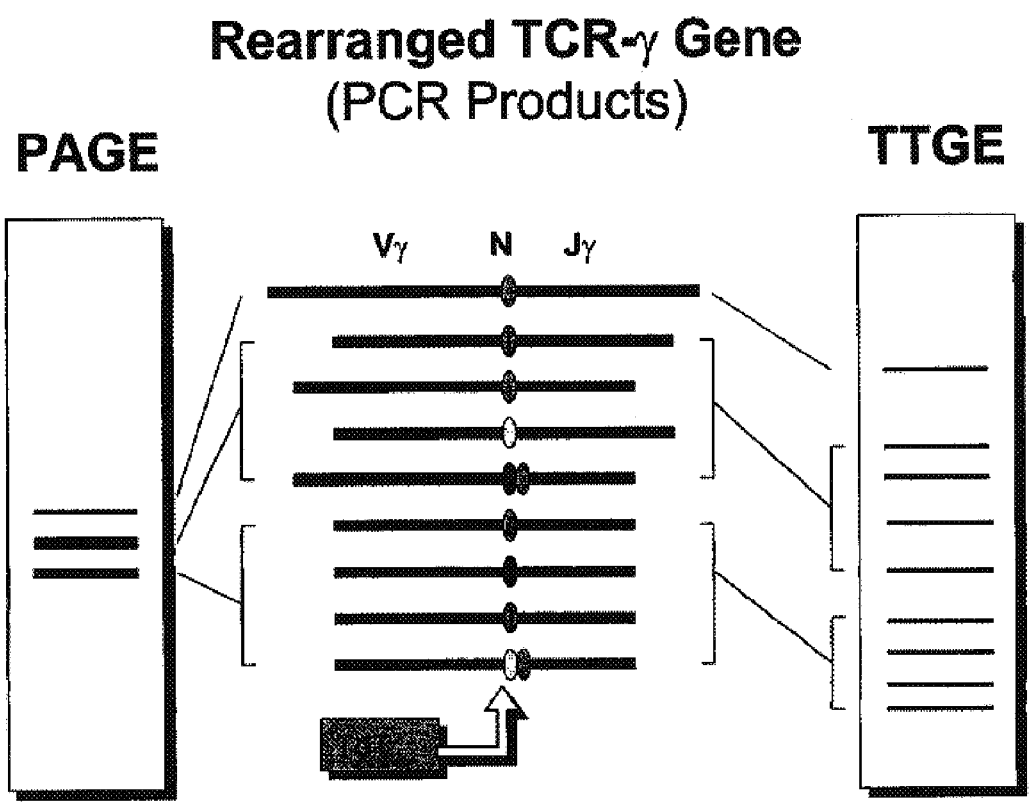
FIG. 1 depicts schematically the resolving power of TTGE versus PAGE in analyzing rearranged TCR-γ gene rearrangements.

For PAGE, the samples were run for 1 hour at 90 volts. PAGE analysis of the PCR products shows that 10 of the 42 samples amplified with Vγ1–8 +Jγ½ primers yield a discrete single band of approximately 200 bp superimposed on a background smear (FIG. 1). These samples are presumed to contain monoclonal T-cells. The other 32 samples yield either a smear or a cluster of PCR products mixed with a background smear of a similar intensity. These samples are classified as containing only polyclonal T-cells.

For TTGE, the samples were electrophoresed for 6 hours at 90 volts on an 8% polyacrylamide gel (37.5:1) containing 1.75 M urea and 10% formamide in 1×TAE buffer (40 mM Tris base, 20 mM glacial acetic acid, 1 mM EDTA, pH 8.0). The electrophoretic temperatures are determined based on the melting profiles of the PCR fragments to be analyzed using WinMelt™ DNA melting profile analysis software fiom Bio-Rad Laboratories (Hercules, Calif., USA). In one run, the temperature was uniformly increased from 60° C. to 66° C. at a ramp rate of 1° C. per hour. Gels were removed, stained with ethidium bromide (1 µg/ml) for 15 min, destained with water for 1 min and photographed under UV light using Chemilmager™ 4400 Alpha Imager from Alpha Innotech Corporation (San Leandro, Calif., USA).

TTGE analysis of the PCR products resulted in 2 distinct patterns (FIG. 1). The first pattern was a faint smear visible throughout the gel lane. This is characteristic of rearranged V-J fragments amplified from polyclonal T-cell populations without a predominant clone. Of the 42 samples tested, 28 shows such a pattern. The second pattern was one or more discrete bands with significantly stronger intensity compared to the faint background smear. These cases represent clonally rearranged TCR-γ gene. Of the 42 samples, 14 amplified with Vγ1–8+Jγ½ primers show clonal rearrangements of TCR-γ gene.

TCR-γ gene rearrangement involves recombination between one of the V regions (Vγ1–8, Vγ9, Vγ10 and Vγ11) and one of the J regions (Jγ½ and JγP½). Primers Vγ1–8 for V region and Jγ½ for J region were used to analyze the most common VJγ recombination types for method comparison between PCR/PAGE and PCR/TTGE. Most samples with predominant clones displayed a single band for the Vγ1–8+Jγ½ primer set. Such a single band reflects monoallelic VJγ rearrangement at the analyzed V and J location.

Among the 14 samples positive by PCR/TTGE, two samples showed multiple bands. One sample shows two discrete bands of rearranged TCR-γ gene amplicon reflecting biallelic VJγ rearrangement with two homoduplexes. One sample shows four discrete bands which represent another form of biallelic VJγ rearrangement with two heteroduplexes at the upper position and two homoduplexes at the lower position.

Among the other 12 samples with a single predominant TCR-γ gene band with Vγ1–8+Jγ½ primers, ten were found to posses another type of VJγ rearrangement when analyzed using Vγ11+Jγ½ primer set which detects rearrangements between Vγ11 and Jγ½ regions (data not shown). This finding suggests that at least 86% ($^{12}/_{14}$) of the clonal VJγ rearrangements are biallelic heterozygosity, i.e., the predominant clonal T-cells carried two different TCR-γ gene alleles with different VJγ rearrangements. Similar results have been previously described by others (Theodorou el al., Blood 86: 305–310, 1995; Menke et al., Electrophoresis 16: 733–738, 1995).

Multiple bands found on a TTGE gel should be interpreted with caution since they may reflect the following possibilities: 1) Biallelic VJγ rearrangement between Vγ1–8 and Jγ½ regions analyzed with two heteroduplexes and two homoduplexes or with two homoduplexes only. The former is a typical pattern for two different DNA molecules with minor base pair substitution(s) while the latter may reflect two types of DNA molecules too distinct to form heteroduplex structures. In one of the aspects of the present invention, at least two bands should display similar signal intensity. Similar situations have been reported by others using DGGE method (Theodorou et al., Blood 86: 305–310, 1995; Anderson et al., J. Cutan Pathol 26: 176–182, 1999); 2) Non-specific PCR amplification under certain circumstances resulting in artificial DNA bands; and 3) Multiclonal T-cell evolution in the samples.

As shown in Table 1, comparison of the two methods shows that 8 samples positive by PCR/PAGE are also positive by PCR/TTGE and 26 samples negative by PCR/PAGE are also negative by PCR/TTGE (81% concordance). In addition, two samples positive by PCR/PAGE are negative by PCR/TTGE and six samnples negative by PCR/PAGE are positive by PCR/TTGE (19% discordance).

Of the 6 cases negative with PCR/PAGE and positive with PCR/TTGE, five are subsequently diagnosed as having T-cell lymphoma based on clinical features and pathologic findings, and the other patient show persistent skin rashes suspicious for cutaneous T-cell lymphoma (Table 2). The two patients whose samples are positive with PCR/PAGE and negative with PCR/TTGE do not show any overt evidence of malignancy (Table 2) at the time of the experiments.

Example 5

Sensitivity, Specificity, Reproducibility and Stability Assayfor TTGE Analysis

The lower limit of detection (sensitivity) of the PCR/TTGE assay for clonal T-cell receptor-γ gene rearrangement is tested using cloned TCR-γ gene standard DNA serially diluted ten-fold in human normal genomic DNA. The concentration of the positive standard DNA was measured by a spectrophotometer, and the DNA molecule copy number per $\mu l$ is calculated based on the theoretical molecular weight of the DNA clone (the cloning vector+the target insert≈2,480,000). About $10^8$, $10^7$, $10^6$, $10^5$, $10^4$, $10^3$, $10^2$, 0 standard DNA molecules was spiked into $10^7$ human normal genomic DNA (~1 $\mu g$) to form clonal TCR-γ gene/normal genomic DNA (P/N) ratios of $10^1$, $10^0$, $10^{-1}$, $10^{-2}$, $10^{-3}$, $10^{-4}$, $10^{-5}$, 0 respectively. The mixed DNA samples were amplified and analyzed using the PCR/TTGE method described above.

Figure 2:
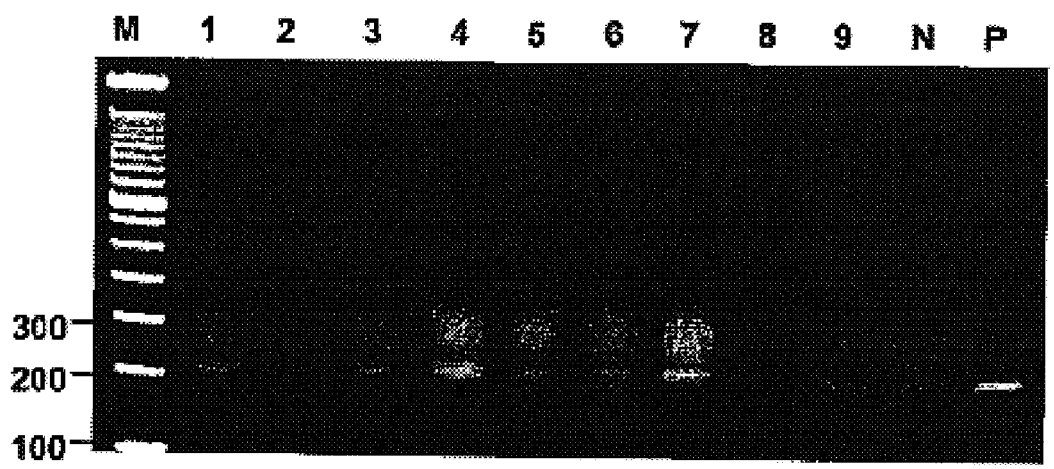
FIG. 2 depicts the detection of clonal TCR-γ gene rearrangement in clinical samples by PCR/PAGE (upper panel)
Figure 2:
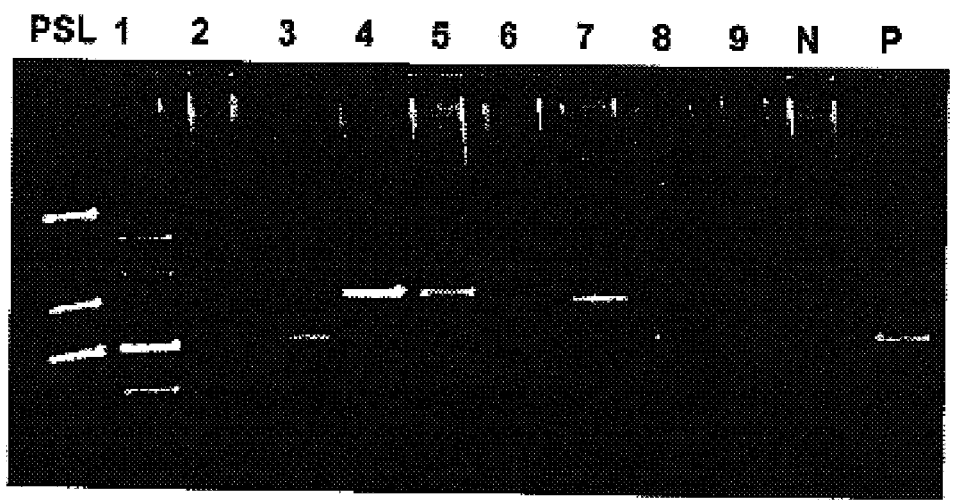

To compare the specificity of the method of PCR/PAGE with PCR/TTGE for detecting clonal TCR-γ rearrangements, one positive sample DNA was serially diluted two-fold with negative standard DNA. The diluted samples were then amplified by PCR and analyzed by both PAGE and TTGE (FIG. 2).

The sensitivity study shows that PCR/TTGE can detect clonal TCR-γ gene at P/N ratios as low as $10^{-2}$ which is equivalent to one malignant T-cell among 100 normal cells. This result is similar to that reported by Theodorou et al who tested DNA from the Jurkat T-cell line with a biallelic Vγ1–8+Jγ½ and Vγ11+Jγ½ rearrangements diluted in DNA from normal skin. Using the PCR/DGGE method, Theodorou et al reported a detectable signal at 1% to 0.1% dilution range (Theodorou et al. Blood 86: 305–310, 1995). In the comparison of specificity between PCR/PAGE and PCR/TTGE (FIG. 2), the negative standard (N) shows no band on TTGE gel while the serially diluted samples show progressively decreased signals on TTGE gel with progressive dilutions. By contrast, on PAGE, the known negative standard (N) shows a ~200 bp band, which is difficult to distinguish from the bands in the positive samples, while the serially diluted samples do not show significant change in signal intensity.

Intra-assay variability and inter-assay variability were evaluated respectively by testing 10 clinical samples in triplicate and by testing the same three samples three times on different days. The sample stability study is carried out by testing blood samples stored at different temperature conditions (~4° C. and room temperature) for different periods of time (1–7 days).

The results from the intra-assay and inter-assay variability studies do not show significant variability of the band pattern and signal intensity. The sample stability study shows that DNA extracted from samples stored at 4° C. for up to 7 days and at room temperature for up to 4 days can be used for PCR amplification to generate TCR-γ gene amplicons for TCR-γ gene rearrangement analysis by TTGE without significant variability of the band pattern and signal intensity.

Due to the high sensitivity of TTGE, non-specific bands may be visible in the negative standard and the samples with low population of predominant T-cell clone. These bands, however, are usually invisible or very faint in samples with strong TCR-γ gene clonal band(s) which migrate(s) at different position(s). Such artificial bands should be disregarded in order to avoid false positive results.

TABLE 1

Comparison between PCR/PAGE and PCR/TTGE for TCR-γ gene rearrangement between Vγ1-8 and Jγ1/2.

| | PCR/TTGE | | |
| --- | --- | --- | --- |
| PCR/PAGE | Positive | Negative | Total |
| Positive | 8 | 2 | 10 |
| Negative | 6 | 26 | 32 |
| Total | 14 | 28 | 42 |

Concordance: 81%
Discrepancy: 19%

TABLE 2

Correlation between the test results and clinical diagnosis for samples with discrepancy

| No | Sample Type | PCR/PAGE | PCR/TTGE | Clinical Diagnosis |
| --- | --- | --- | --- | --- |
| 1 | EDTA Whole Blood | − | + | T-cell Lymphoma |
| 2 | EDTA Whole Blood | − | + | T-cell Lymphoma |
| 3 | Lymph Node Tissue | − | + | T-cell Lymphoma |
| 4 | Lymph Node Tissue | − | + | T-cell Lymphoma |
| 5 | Lymph Node Tissue | − | + | Suspicious for malignancy |
| 6 | EDTA Whole Blood | − | + | T-cell Lymphoma |
| 7 | EDTA Whole Blood | + | − | Lymphocytosis |
| 8 | EDTA Whole Blood | + | − | Lymphocytosis |

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the feaures shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

What is claimed is:

1. A method for determining the clonality of a T-cell receptor (TCR) rearrangement in a sample, comprising:

extracting nucleic acid from said sample;

amplifying said nucleic acid by polymerase chain reaction (PCR) with two or more TCR-specific primers to provide one or more TCR DNA fragments; and analyzing said TCR DNA fragments using an electrophoretic gel by temporal temperature gradient gel electrophoresis (TTGE), wherein the presence of one or more discrete DNA bands in said electrophoretic gel indicates the presence of a clonal TCR rearrangement, wherein said TCR-specific primers are the DNA sequences set forth in SEQ ID NO:3 and SEQ ID NO:4.

* * * * *

SEQUENCE LISTING

<160> NUMBER OF SEQ ID NOS: 8

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 1
gtgctgcagg tgtaaacttg taccag                                    26

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 2
cacggatccg gtagcagcgg tagagttg                                  28

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
agggttgtgt tggaatcagg                                           20

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Primer

<400> SEQUENCE: 4
cgcccgccgc gccccgcgcc cgtcccgccg ccccctgtt ccactgccaa agagtttctt    60

```
<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 5
taaattccaa attcttggtt ta                                          22

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 6
ctcaacaaaa tccgcagctc gacgcagca                                   29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 7
caatctctgc tcaagattgc tcaggtggg                                   29

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
actctgcagc tcttgggca ctgctctaaa                                   30
```